US010443385B2

(12) United States Patent
Diwinsky et al.

(10) Patent No.: US 10,443,385 B2
(45) Date of Patent: Oct. 15, 2019

(54) IN SITU GAS TURBINE PREVENTION OF CRACK GROWTH PROGRESSION VIA LASER WELDING

(71) Applicant: General Electric Company, Schenectady, NY (US)

(72) Inventors: David Scott Diwinsky, West Chester, OH (US); Herbert Chidsey Roberts, Middletown, OH (US)

(73) Assignee: General Electric Company, Schenectady, NY (US)

( * ) Notice: Subject to any disclaimer, the term of this patent is extended or adjusted under 35 U.S.C. 154(b) by 279 days.

(21) Appl. No.: 15/014,095

(22) Filed: Feb. 3, 2016

(65) Prior Publication Data

US 2017/0218763 A1  Aug. 3, 2017

(51) Int. Cl.
*F01D 5/00* (2006.01)
*B23K 26/08* (2014.01)
(Continued)

(52) U.S. Cl.
CPC ............ *F01D 5/005* (2013.01); *B23K 26/032* (2013.01); *B23K 26/0884* (2013.01);
(Continued)

(58) Field of Classification Search
CPC .......... F01D 5/005; B23P 6/045; B23P 6/007; B23K 26/342; B23K 26/144;
(Continued)

(56) References Cited

U.S. PATENT DOCUMENTS 2,011,484 A    8/1935  Harman
2,252,986 A    8/1941  Scott
(Continued)

FOREIGN PATENT DOCUMENTS

CN      2760614 Y    2/2006
CN    101342628 A    1/2009
(Continued)

OTHER PUBLICATIONS

Extended European Search Report and Opinion issued in connection with corresponding EP Application No. 17153816.8 dated Jul. 10, 2017.
(Continued)

*Primary Examiner* — Ryan J. Walters
*Assistant Examiner* — Lawrence Averick
(74) *Attorney, Agent, or Firm* — Dority & Manning, P.A.

(57) ABSTRACT

Methods for material build-up on a tip of a blade of a gas turbine engine are provided. The method can include inserting a material supply adjacent to the tip and directing a laser onto the interface of the material supply and the tip such that the material supply melts and attaches to the tip. Methods are also provided for remotely stopping a crack in a component of a gas turbine engine. The method can include inserting an integrated repair interface attached to a cable delivery system within a gas turbine engine; positioning the tip adjacent to a defect within a surface of the component; supplying a new material to the fillable area to fill the defect; and directing a laser to the new material within the fillable area to fuse the new material to the component within the defect.

14 Claims, 7 Drawing Sheets

(51) Int. Cl.
  *B23P 6/00* (2006.01)
  *B23K 26/03* (2006.01)
  *G01N 21/954* (2006.01)
  *B23K 26/342* (2014.01)
  *B23K 26/70* (2014.01)
  *B23K 26/144* (2014.01)
  *B23P 6/04* (2006.01)
  *B23K 101/00* (2006.01)
  *B23K 103/18* (2006.01)

(52) U.S. Cl.
  CPC .......... *B23K 26/144* (2015.10); *B23K 26/342* (2015.10); *B23K 26/702* (2015.10); *B23P 6/007* (2013.01); *B23P 6/045* (2013.01); *G01N 21/954* (2013.01); *B23K 2101/001* (2018.08); *B23K 2103/26* (2018.08); *F05D 2230/234* (2013.01); *F05D 2230/80* (2013.01); *F05D 2260/83* (2013.01)

(58) Field of Classification Search
  CPC .............. B23K 26/702; B23K 26/0884; B23K 26/032; B23K 2201/001; B23K 2203/26; F05D 2260/83; F05D 2230/80; F05D 2230/234
  See application file for complete search history.

(56) References Cited

U.S. PATENT DOCUMENTS

| | | | |
|---|---|---|---|
| 2,361,106 A | 10/1944 | Jensen | |
| 4,611,744 A | 9/1986 | Fraser et al. | |
| 4,743,733 A | 5/1988 | Mehta et al. | |
| 5,019,429 A * | 5/1991 | Moskowitz | B05B 7/205 427/422 |
| 5,062,904 A * | 11/1991 | Yoden | G11B 5/712 148/105 |
| 5,076,660 A | 12/1991 | Messinger | |
| 5,160,822 A * | 11/1992 | Aleshin | F01D 5/20 219/121.64 |
| 5,302,414 A * | 4/1994 | Alkhimov | B05B 7/144 427/191 |
| 5,741,965 A | 4/1998 | Hernandez et al. | |
| 6,206,067 B1 | 3/2001 | Kociemba et al. | |
| 6,269,540 B1 | 8/2001 | Islam et al. | |
| 6,270,603 B1 | 8/2001 | Westerman et al. | |
| 6,302,625 B1 | 10/2001 | Carey et al. | |
| 6,525,500 B2 | 2/2003 | Hatley et al. | |
| 6,542,230 B1 * | 4/2003 | Luke | B23K 26/032 356/241.1 |
| 6,593,540 B1 | 7/2003 | Baker et al. | |
| 6,620,457 B2 | 9/2003 | Farmer et al. | |
| 6,912,446 B2 | 6/2005 | Wang et al. | |
| 6,919,956 B2 | 7/2005 | Kitagawa et al. | |
| 7,000,303 B2 | 2/2006 | Talwar et al. | |
| 7,016,035 B2 * | 3/2006 | Wu | G01J 3/02 356/318 |
| 7,032,279 B2 | 4/2006 | McCarvill et al. | |
| 7,034,262 B2 | 4/2006 | Fischer et al. | |
| 7,171,279 B2 | 1/2007 | Buckingham et al. | |
| 7,174,797 B2 | 2/2007 | Brostmeyer et al. | |
| 7,278,208 B2 | 10/2007 | LeSaint et al. | |
| 7,392,713 B2 | 7/2008 | Barkhoudarian | |
| 7,449,658 B2 | 11/2008 | Mielke | |
| 7,458,768 B2 | 12/2008 | Dube et al. | |
| 7,499,772 B2 | 3/2009 | Wilcox et al. | |
| 7,513,024 B2 | 4/2009 | Keller | |
| 8,039,773 B2 | 10/2011 | Spallek et al. | |
| 8,181,528 B2 | 3/2012 | Reed et al. | |
| 8,247,722 B2 * | 8/2012 | Ominato | D05B 69/04 200/314 |
| 8,247,733 B2 * | 8/2012 | Zhu | B23K 26/03 219/121.63 |
| 8,348,136 B1 | 1/2013 | Potter et al. | |
| 8,400,501 B2 | 3/2013 | Heyworth et al. | |
| 8,563,080 B2 | 10/2013 | Hopkins | |
| 8,786,300 B2 | 7/2014 | Bendall | |
| 8,801,502 B2 | 8/2014 | Ng et al. | |
| 8,895,887 B2 | 11/2014 | Trapp et al. | |
| 8,904,635 B2 | 12/2014 | Berkebile et al. | |
| 8,910,359 B2 | 12/2014 | Jones et al. | |
| 8,927,897 B2 | 1/2015 | Xu et al. | |
| 9,003,880 B2 | 4/2015 | Sbihli et al. | |
| 9,046,892 B2 | 6/2015 | Jang et al. | |
| 2005/0068524 A1 * | 3/2005 | Wu | G01J 3/02 356/316 |
| 2006/0042083 A1 * | 3/2006 | Baker | B23K 26/0096 29/889.1 |
| 2009/0243176 A1 * | 10/2009 | Alexander | B25B 5/14 269/21 |
| 2010/0176097 A1 * | 7/2010 | Zhu | B23K 26/03 219/121.63 |
| 2012/0000890 A1 | 1/2012 | Ito et al. | |
| 2012/0121382 A1 * | 5/2012 | Xu | F01D 25/002 415/118 |
| 2012/0286109 A1 * | 11/2012 | Clark | F01D 21/003 248/70 |
| 2013/0167375 A1 * | 7/2013 | Roesing | B23P 15/00 29/888.3 |
| 2013/0174869 A1 | 7/2013 | Rösing et al. | |
| 2013/0289766 A1 | 10/2013 | Hafenrichter et al. | |
| 2013/0305508 A1 * | 11/2013 | Sachacht | B23P 6/002 29/402.18 |
| 2013/0316183 A1 * | 11/2013 | Kulkarni, Jr. | B23P 6/007 428/557 |
| 2014/0063228 A1 | 3/2014 | Boles et al. | |
| 2014/0144473 A1 | 5/2014 | Martin | |
| 2014/0202286 A1 * | 7/2014 | Yokoyama | B22F 9/08 75/331 |
| 2014/0223737 A1 | 8/2014 | Kell et al. | |
| 2014/0278221 A1 | 9/2014 | Troy et al. | |
| 2015/0034266 A1 | 2/2015 | Bruck et al. | |
| 2015/0036127 A1 | 2/2015 | Konomura et al. | |
| 2015/0174838 A1 | 6/2015 | Kittleson et al. | |
| 2016/0229005 A1 * | 8/2016 | Ryan | F01D 25/285 |
| 2016/0279722 A1 * | 9/2016 | Capriotti | B23H 3/04 |
| 2016/0318135 A1 * | 11/2016 | Raulerson | F01D 5/005 |
| 2017/0218761 A1 * | 8/2017 | Roberts | B23K 26/032 |
| 2017/0218762 A1 * | 8/2017 | Roberts | F01C 21/10 |
| 2017/0218764 A1 * | 8/2017 | Roberts | F01D 5/005 |
| 2017/0254205 A1 | 9/2017 | Scott et al. | |
| 2017/0326685 A1 * | 11/2017 | Kell | B23K 26/0096 |

FOREIGN PATENT DOCUMENTS

| | | |
|---|---|---|
| DE | 3813157 A1 | 12/1988 |
| DE | 10 2009 004661 A1 | 7/2010 |
| EP | 1609957 A2 | 12/2005 |
| EP | 2711759 A1 | 3/2014 |
| WO | WO00/06336 | 2/2000 |
| WO | WO2005/049263 A1 | 6/2005 |
| WO | WO2013/097944 A1 | 7/2013 |

OTHER PUBLICATIONS

Machine Translation and First Office Action and Search issued in connection with corresponding CN Application No. 201710056205.5 dated May 4, 2018.

Office Action issued in connection with corresponding CA Application No. 2956355 dated Aug. 1, 2018.

* cited by examiner

IN SITU GAS TURBINE PREVENTION OF CRACK GROWTH PROGRESSION VIA LASER WELDING

FIELD OF THE INVENTION

The present subject matter relates generally to gas turbine engines and, more particularly, to a system and method for performing an in situ repair of an internal component of a gas turbine engine.

BACKGROUND OF THE INVENTION

A gas turbine engine typically includes a turbomachinery core having a high pressure compressor, combustor, and high pressure turbine in serial flow relationship. The core is operable in a known manner to generate a primary gas flow. The high pressure compressor includes annular arrays ("rows") of stationary vanes that direct air entering the engine into downstream, rotating blades of the compressor. Collectively one row of compressor vanes and one row of compressor blades make up a "stage" of the compressor. Similarly, the high pressure turbine includes annular rows of stationary nozzle vanes that direct the gases exiting the combustor into downstream, rotating blades of the turbine. Collectively one row of nozzle vanes and one row of turbine blades make up a "stage" of the turbine. Typically, both the compressor and turbine include a plurality of successive stages.

Gas turbine engines, particularly aircraft engines, require a high degree of periodic maintenance. For example, periodic maintenance is often scheduled to allow internal components of the engine to be inspected for defects and subsequently repaired. Unfortunately, many conventional repair methods used for aircraft engines require that the engine be removed from the body of the aircraft and subsequently partially or fully disassembled. As such, these repair methods result in a significant increase in both the time and the costs associated with repairing internal engine components.

Accordingly, a system and method for performing an in situ repair of an internal component of a gas turbine engine would be welcomed within the technology.

BRIEF DESCRIPTION OF THE INVENTION

Aspects and advantages of the invention will be set forth in part in the following description, or may be obvious from the description, or may be learned through practice of the invention.

Methods are generally provided for material build-up on a tip of a blade of a gas turbine engine. In one embodiment, the method includes inserting a material supply adjacent to the tip and directing a laser onto the interface of the material supply and the tip such that the material supply melts and attaches to the tip.

Methods are also generally provided for remotely stopping a crack in a component of a gas turbine engine. In one embodiment, the method includes inserting an integrated repair interface attached to a cable delivery system within a gas turbine engine; positioning the tip adjacent to a defect within a surface of the component; supplying a new material to the fillable area to fill the defect; and directing a laser to the new material within the fillable area to fuse the new material to the component within the defect.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended Figs., in which.

Figure 1:
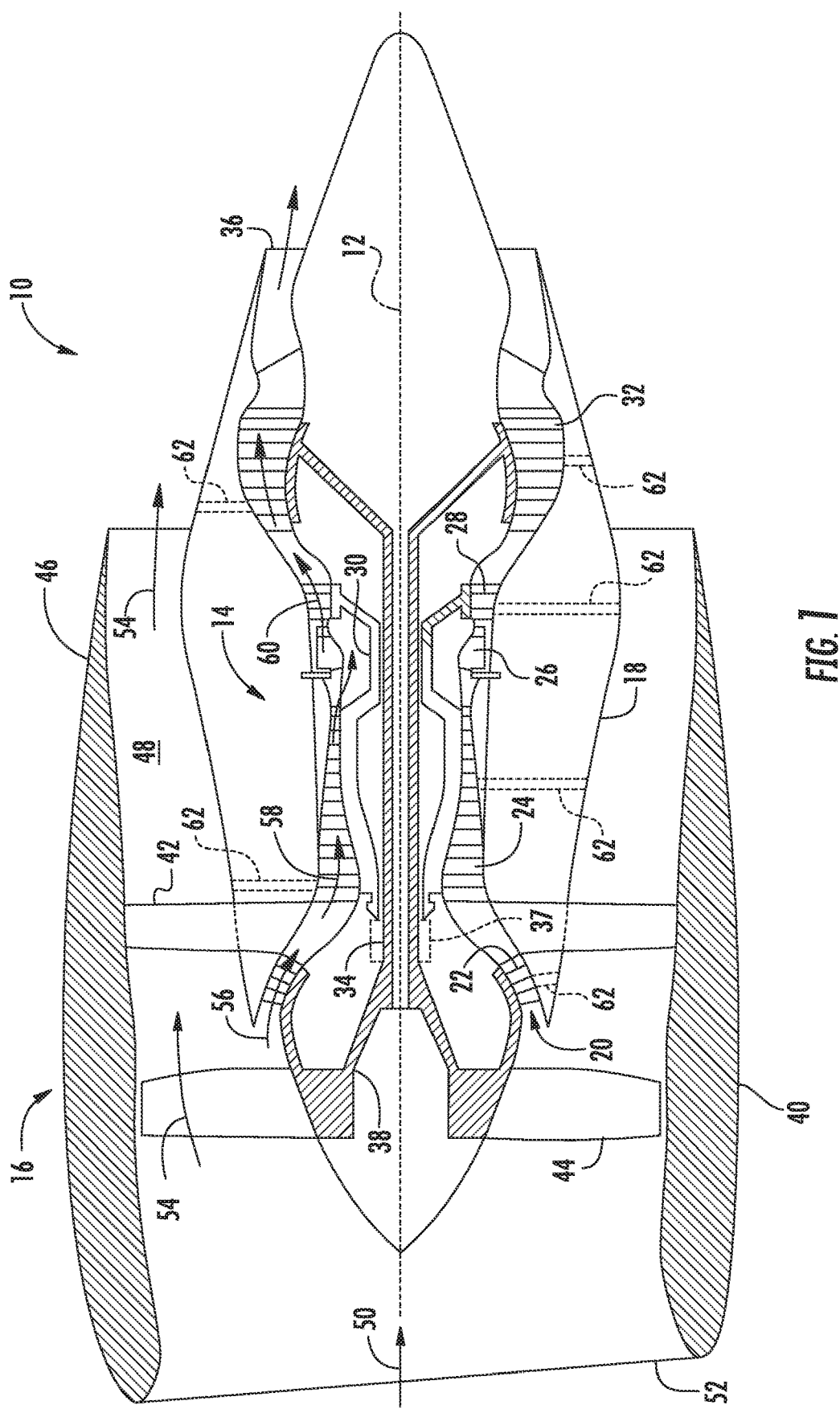
FIG. 1 illustrates a cross-sectional view of one embodiment of a gas turbine engine that may be utilized within an aircraft in accordance with aspects of the present subject matter.

Repeat use of reference characters in the present specification and drawings is intended to represent the same or analogous features or elements of the present invention.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "first", "second", and "third" may be used interchangeably to distinguish one component from another and are not intended to signify location or importance of the individual components.

The terms "upstream" and "downstream" refer to the relative direction with respect to fluid flow in a fluid pathway. For example, "upstream" refers to the direction from which the fluid flows, and "downstream" refers to the direction to which the fluid flows.

In general, a system and method is provided for performing an in situ repair of an internal component of a gas turbine engine. In several embodiments, the system may include a repair tool configured to be inserted through an access port of the gas turbine engine to allow a repair tip or tip end of the tool to be positioned adjacent to a defect of an internal component of the engine, such as a crack, void, distressed area or any other defect defining a fillable volume. As will be described below, the repair tool may be configured to temporarily attach to the surface of the component, allowing precision work to be performed on the component. For example, the repair tool can supply a new material (solid or liquid) and direct a laser to heat to fuse new material within the crack to repair the defect. For example, if the new material is supplied as a solid, then the laser can heat and weld the material within the crack to repair the defect.

It should be appreciated that the disclosed system and method may generally be used to perform in situ repairs of internal components located within any suitable type of gas turbine engine, including aircraft-based turbine engines and land-based turbine engines, regardless of the engine's current assembly state (e.g., fully or partially assembled). Additionally, with reference to aircraft engines, it should be appreciated that the present subject matter may be implemented on-wing or off-wing.

Referring now to the drawings, FIG. 1 illustrates a cross-sectional view of one embodiment of a gas turbine engine 10 that may be utilized within an aircraft in accordance with aspects of the present subject matter, with the engine 10 being shown having a longitudinal or axial centerline axis 12 extending therethrough for reference purposes. In general, the engine 10 may include a core gas turbine engine (indicated generally by reference character 14) and a fan section 16 positioned upstream thereof. The core engine 14 may generally include a substantially tubular outer casing 18 that defines an annular inlet 20. In addition, the outer casing 18 may further enclose and support a booster compressor 22 for increasing the pressure of the air that enters the core engine 14 to a first pressure level. A high pressure, multi-stage, axial-flow compressor 24 may then receive the pressurized air from the booster compressor 22 and further increase the pressure of such air. The pressurized air exiting the high-pressure compressor 24 may then flow to a combustor 26 within which fuel is injected into the flow of pressurized air, with the resulting mixture being combusted within the combustor 26. The high energy combustion products are directed from the combustor 26 along the hot gas path of the engine 10 to a first (high pressure) turbine 28 for driving the high pressure compressor 24 via a first (high pressure) drive shaft 30, and then to a second (low pressure) turbine 32 for driving the booster compressor 22 and fan section 16 via a second (low pressure) drive shaft 34 that is generally coaxial with first drive shaft 30. After driving each of turbines 28 and 32, the combustion products may be expelled from the core engine 14 via an exhaust nozzle 36 to provide propulsive jet thrust.

Additionally, as shown in FIG. 1, the fan section 16 of the engine 10 may generally include a rotatable, axial-flow fan rotor assembly 38 that is configured to be surrounded by an annular fan casing 40. It should be appreciated by those of ordinary skill in the art that the fan casing 40 may be configured to be supported relative to the core engine 14 by a plurality of substantially radially-extending, circumferentially-spaced outlet guide vanes 42. As such, the fan casing 40 may enclose the fan rotor assembly 38 and its corresponding fan rotor blades 44. Moreover, a downstream section 46 of the fan casing 40 may extend over an outer portion of the core engine 14 so as to define a secondary, or by-pass, airflow conduit 48 that provides additional propulsive jet thrust.

It should be appreciated that, in several embodiments, the second (low pressure) drive shaft 34 may be directly coupled to the fan rotor assembly 38 to provide a direct-drive configuration. Alternatively, the second drive shaft 34 may be coupled to the fan rotor assembly 38 via a speed reduction device 37 (e.g., a reduction gear or gearbox) to provide an indirect-drive or geared drive configuration. Such a speed reduction device(s) may also be provided between any other suitable shafts and/or spools within the engine 10 as desired or required.

During operation of the engine 10, it should be appreciated that an initial air flow (indicated by arrow 50) may enter the engine 10 through an associated inlet 52 of the fan casing 40. The air flow 50 then passes through the fan blades 44 and splits into a first compressed air flow (indicated by arrow 54) that moves through conduit 48 and a second compressed air flow (indicated by arrow 56) which enters the booster compressor 22. The pressure of the second compressed air flow 56 is then increased and enters the high pressure compressor 24 (as indicated by arrow 58). After mixing with fuel and being combusted within the combustor 26, the combustion products 60 exit the combustor 26 and flow through the first turbine 28. Thereafter, the combustion products 60 flow through the second turbine 32 and exit the exhaust nozzle 36 to provide thrust for the engine 10.

The gas turbine engine 10 may also include a plurality of access ports defined through its casings and/or frames for providing access to the interior of the core engine 14. For instance, as shown in FIG. 1, the engine 10 may include a plurality of access ports 62 (only six of which are shown) defined through the outer casing 18 for providing internal access to one or both of the compressors 22, 24 and/or for providing internal access to one or both of the turbines 28, 32. In several embodiments, the access ports 62 may be spaced apart axially along the core engine 14. For instance, the access ports 62 may be spaced apart axially along each compressor 22, 24 and/or each turbine 28, 32 such that at least one access port 62 is located at each compressor stage and/or each turbine stage for providing access to the internal components located at such stage(s). In addition, the access ports 62 may also be spaced apart circumferentially around the core engine 14. For instance, a plurality of access ports 62 may be spaced apart circumferentially around each compressor stage and/or turbine stage.

It should be appreciated that, although the access ports 62 are generally described herein with reference to providing internal access to one or both of the compressors 22, 24 and/or for providing internal access to one or both of the turbines 28, 32, the gas turbine engine 10 may include access ports 62 providing access to any suitable internal location of the engine 10, such as by including access ports 62 that provide access within the combustor 26 and/or any other suitable component of the engine 10.

Figure 2:
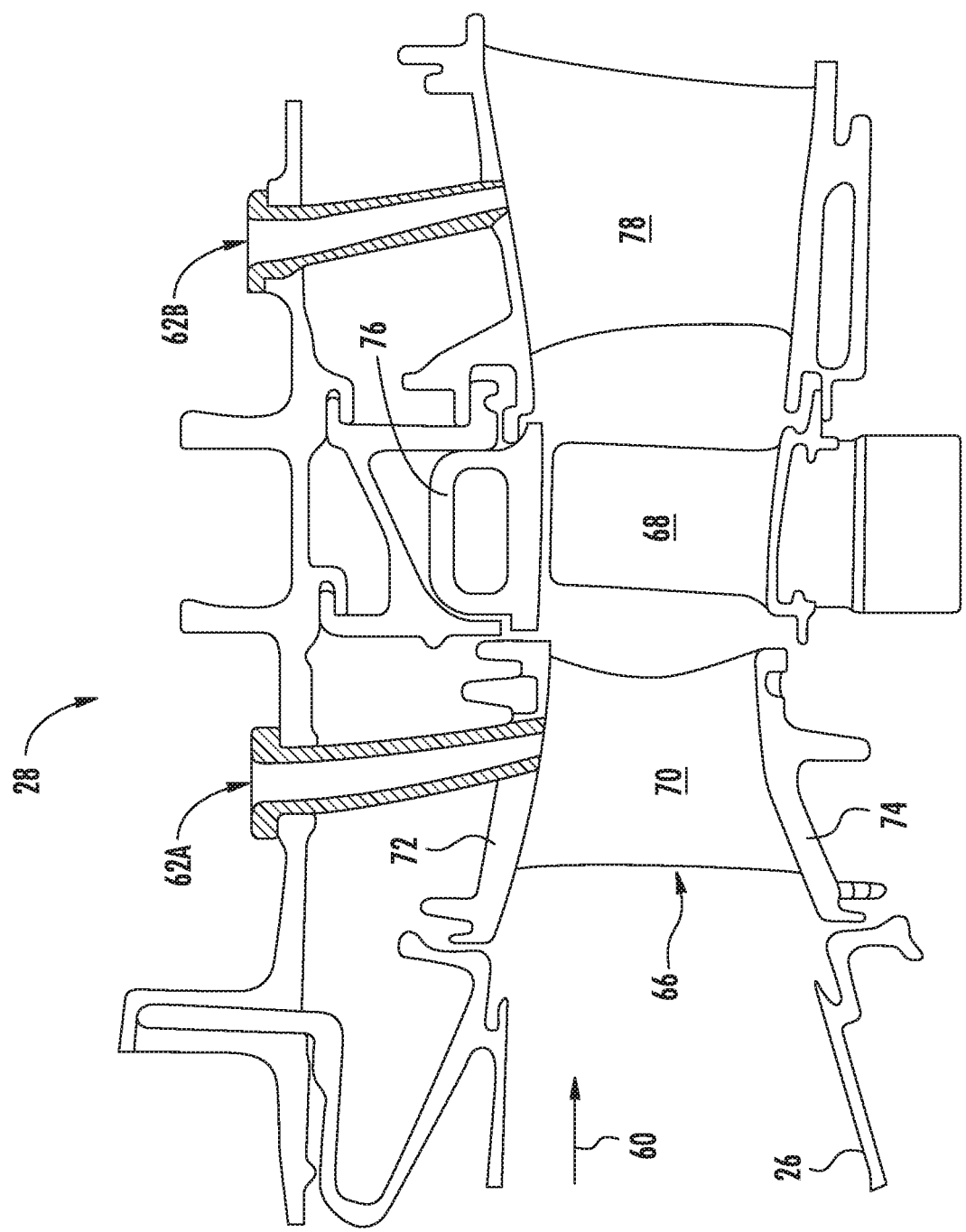
FIG. 2 illustrates a partial, cross-sectional view of one embodiment of a turbine suitable for use within the gas turbine engine shown in FIG. 1, particularly illustrating access ports defined in the engine for providing internal access to the turbine.

Referring now to FIG. 2, a partial, cross-sectional view of the first (or high pressure) turbine 28 described above with reference to FIG. 1 is illustrated in accordance with embodiments of the present subject matter. As shown, the first turbine 28 may include a first stage turbine nozzle 66 and an annular array of rotating turbine blades 68 (one of which is shown) located immediately downstream of the nozzle 66. The nozzle 66 may generally be defined by an annular flow channel that includes a plurality of radially-extending, circularly-spaced nozzle vanes 70 (one of which is shown). The vanes 70 may be supported between a number of arcuate outer bands 72 and arcuate inner bands 74. Additionally, the circumferentially spaced turbine blades 68 may generally be configured to extend radially outwardly from a rotor disk (not shown) that rotates about the centerline axis 12 (FIG. 1) of the engine 10. Moreover, a turbine shroud 76 may be positioned immediately adjacent to the radially outer tips of the turbine blades 68 so as to define the outer radial flowpath boundary for the combustion products 60 flowing through the turbine 28 along the hot gas path of the engine 10.

As indicated above, the turbine 28 may generally include any number of turbine stages, with each stage including an annular array of nozzle vanes and follow-up turbine blades 68. For example, as shown in FIG. 2, an annular array of nozzle vanes 78 of a second stage of the turbine 28 may be located immediately downstream of the turbine blades 68 of the first stage of the turbine 28.

Moreover, as shown in FIG. 2, a plurality of access ports 62 may be defined through the turbine casing and/or frame, with each access port 62 being configured to provide access to the interior of the turbine 28 at a different axial location. Specifically, as indicated above, the access ports 62 may, in several embodiments, be spaced apart axially such that each access port 62 is aligned with or otherwise provides interior access to a different stage of the turbine 28. For instance, as shown in FIG. 2, a first access port 62A may be defined through the turbine casing/frame to provide access to the first stage of the turbine 28 while a second access port 62B may be defined through the turbine casing/frame to provide access to the second stage of the turbine 28.

It should be appreciated that similar access ports 62 may also be provided for any other stages of the turbine 28 and/or for any turbine stages of the second (or low pressure) turbine 32. It should also be appreciated that, in addition to the axially spaced access ports 62 shown in FIG. 2, access ports 62 may be also provided at differing circumferentially spaced locations. For instance, in one embodiment, a plurality of circumferentially spaced access ports may be defined through the turbine casing/frame at each turbine stage to provide interior access to the turbine 28 at multiple circumferential locations around the turbine stage.

Figure 3:
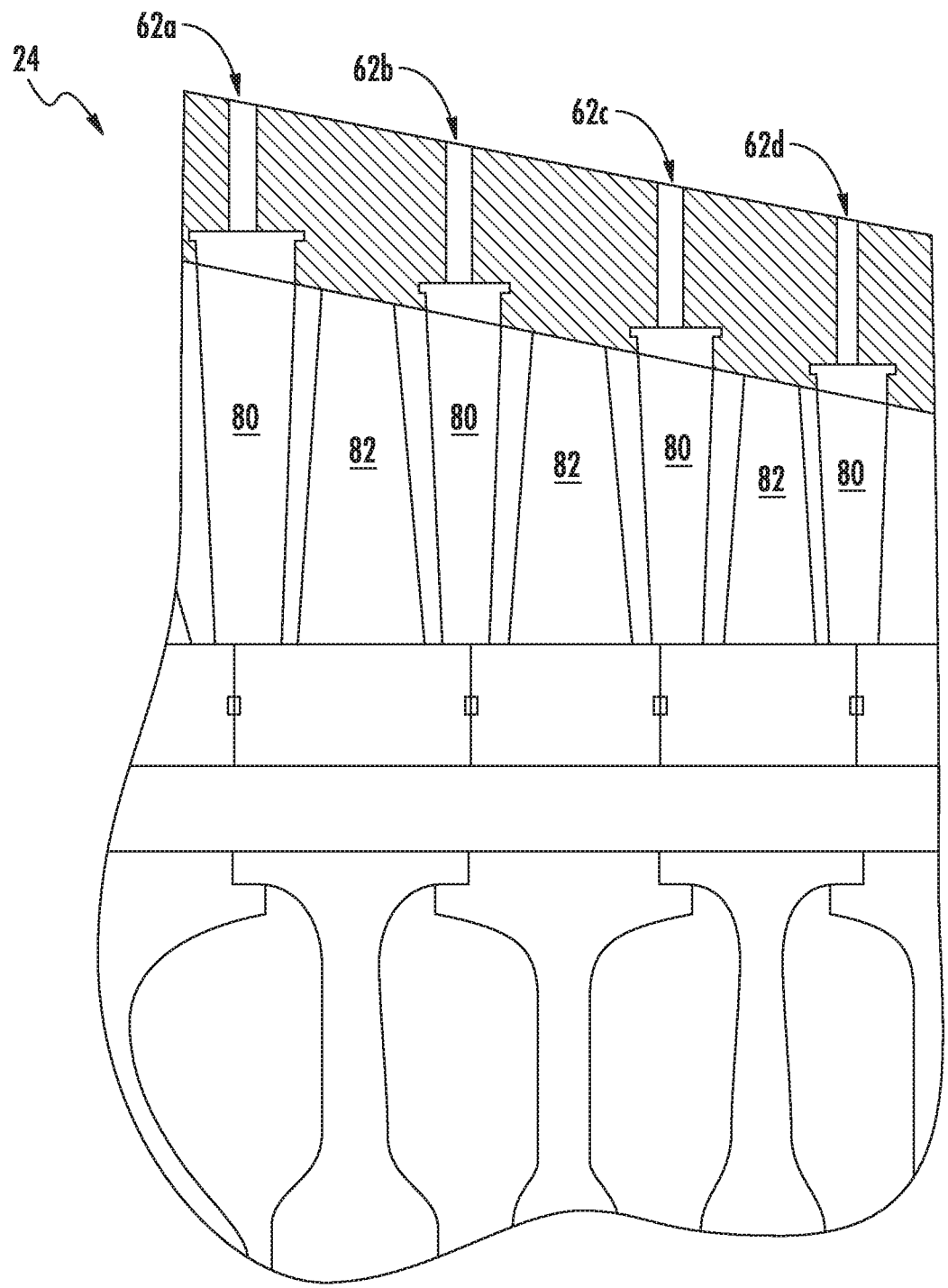
FIG. 3 illustrates a partial, cross-sectional view of one embodiment of a compressor suitable for use within the gas turbine engine shown in FIG. 1, particularly illustrating access ports defined in the engine for providing internal access to the compressor.

Referring now to FIG. 3, a partial, cross-sectional view of the high pressure compressor 24 described above with reference to FIG. 1 is illustrated in accordance with embodiments of the present subject matter. As shown, the compressor 24 may include a plurality of compressor stages, with each stage including both an annular array of fixed compressor vanes 80 (only one of which is shown for each stage) and an annular array of rotatable compressor blades 82 (only one of which is shown for each stage). Each row of compressor vanes 80 is generally configured to direct air flowing through the compressor 24 to the row of compressor blades 82 immediately downstream thereof.

Moreover, the compressor 24 may include a plurality of access ports 62 defined through the compressor casing/frame, with each access port 62 being configured to provide access to the interior of the compressor 24 at a different axial location. Specifically, in several embodiments, the access ports 62 may be spaced apart axially such that each access port 62 is aligned with or otherwise provides interior access port 62 to a different stage of the compressor 24. For instance, as shown in FIG. 3, first, second, third and fourth access ports 62a, 62b, 62c, 62d are illustrated that provide access to four successive stages, respectively, of the compressor 24.

It should be appreciated that similar access ports 62 may also be provided for any of the other stages of the compressor 24 and/or for any of the stages of the low pressure compressor 22. It should also be appreciated that, in addition to the axially spaced access ports 62 shown in FIG. 3, access ports 62 may be also provided at differing circumferentially spaced locations. For instance, in one embodiment, a plurality of circumferentially spaced access ports may be defined through the compressor casing/frame at each compressor stage to provide interior access to the compressor 24 at multiple circumferential locations around the compressor stage.

Figure 4:
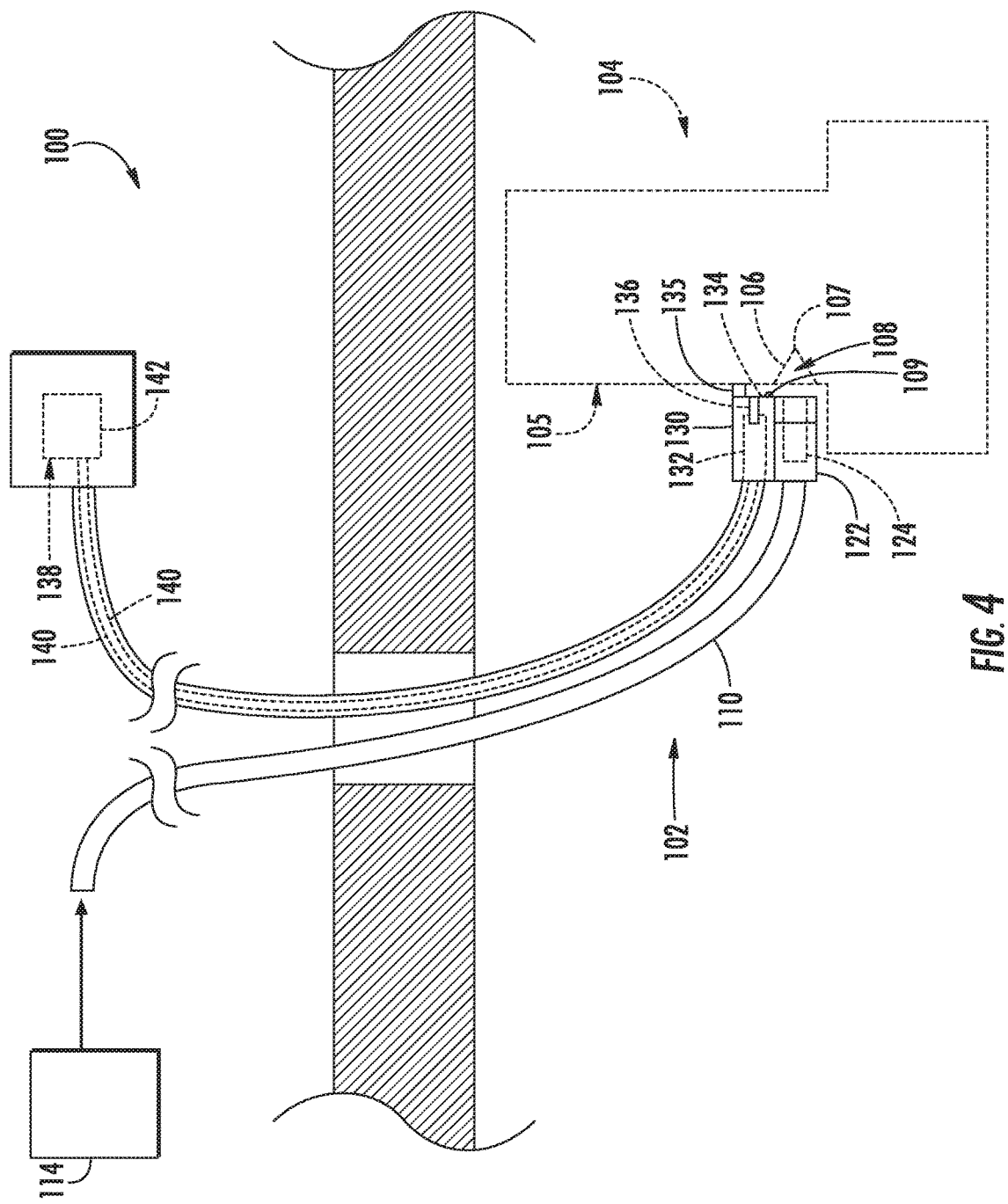
FIG. 4 illustrates a simplified view of one embodiment of a system for performing an in situ repair of an internal component of a gas turbine engine in accordance with aspects of the present subject matter, particularly illustrating a repair tool inserted through an access port of the engine to access a defect of the internal component.

Referring now to FIG. 4, a simplified view of one embodiment of a system 100 for performing an in situ repair of an internal component of a gas turbine engine 10 are illustrated in accordance with aspects of the present subject matter. As shown, the system 100 may include a repair tool 102 configured to be inserted through an access port 62 of the gas turbine engine 10, such as any of the access ports 62 described above with reference to FIGS. 1-3, to allow an in situ repair procedure to be performed on an internal component(s) (indicated by dashed lines 104) of the engine 10.

In general, the repair tool 102 may correspond to any suitable tool(s) and/or component(s) that may be inserted through an access port 62 of the gas turbine engine 10 and attach onto the surface 105 of the component 104 to perform precision work thereon. For example, an attachment mechanism 135 can temporarily attach onto the surface 105 so that the tool 102 can perform work at or near an identified defect 106 of the internal engine component(s) 104 being repaired (e.g., a turbine blade(s)). As such, the repair tool 102 may be temporarily attached to the surface 105 so as to allow for precision work at the defect 106 (e.g., with precision accuracy within about 0.5 mm or less, such as about 0.25 mm or less). As generically shown in FIG. 4, a conduit 110 is attached to a working head 122 includes a work mechanism 124 controllable via a controller 114 (e.g., a computer or other programmable machine).

Figure 5:
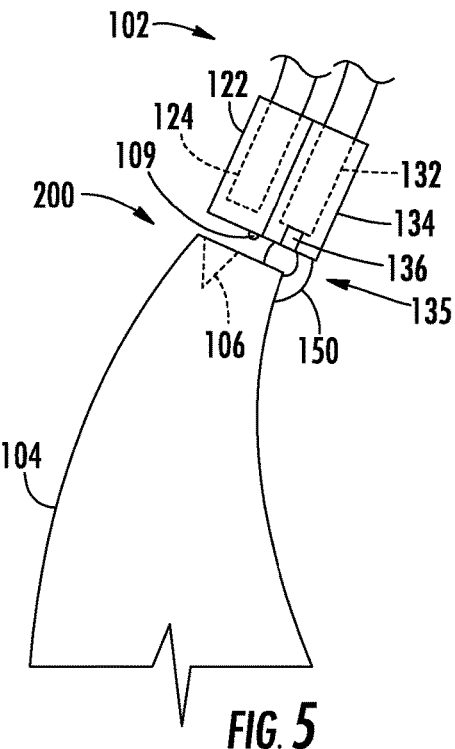
FIG. 5 illustrates a partial view of an exemplary repair tool temporarily secured to a tip of an airfoil in order to perform an in situ repair thereon.

In one embodiment, the attachment mechanism 135 can be a tripod grip for a component 104 having a known shape and/or size. FIG. 5 illustrates a partial view of an exemplary repair tool temporarily secured to a tip of an airfoil in order to perform an in situ repair thereon such that the material supply is positioned between the tip 200 of the blade and a shroud 76. As shown in FIG. 5, the component 104 is an airfoil tip 200 with a known shape and size (e.g., a nozzle and/or blade). In other embodiments, the component 104 can be a trailing edge and/or leading edge of the airfoil. The attachment mechanism 135 includes a plurality of grip arms 150 that attach the repair tool 102 onto the surface 105. The grip arms 150 are bought together onto the edge of the tip 200 until the repair tool 102 is secured onto the tip 200. In the embodiment shown, three grip arms 150 are included in the attachment mechanism 135, although any suitable number of grip arms 150 may be utilized (e.g., three or more grip arms).

Figure 6:
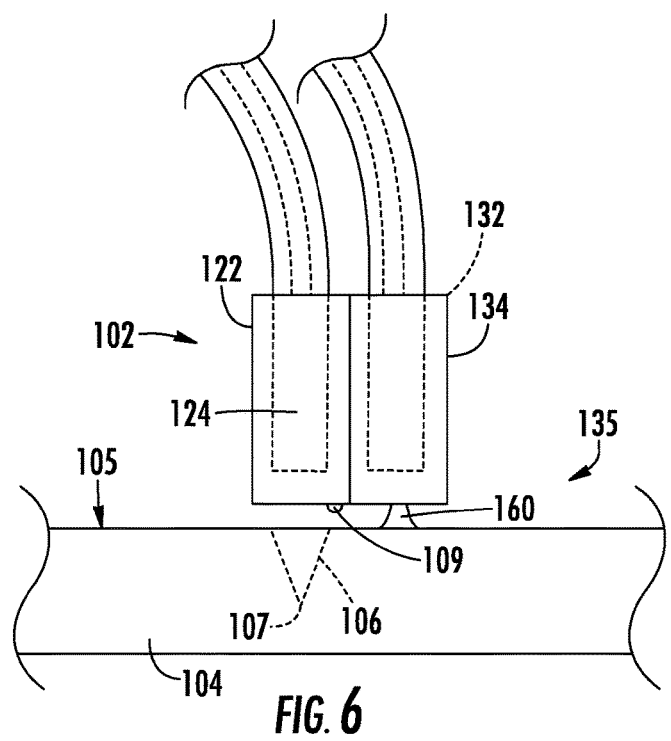
FIG. 6 illustrates a partial view of another exemplary repair tool temporarily secured to a tip of an airfoil in order to perform an in situ repair thereon.

In another embodiment, the attachment mechanism 135 can be a suction cup attached onto the repair tool 102. As shown in FIG. 6, the attachment mechanism 135 includes a suction cup 160 that attach the repair tool 102 onto the surface 105. In one embodiment, a vacuum can be applied within the suction cup 160 to hold the repair tool 102 onto the surface in place. The suction cup 160 can be constructed of a deformable, air-impervious material (e.g., a rubber material) that can form a suction attachment with the surface 105. Although shown with one suction cup 160, any number of suction cups can be utilized to secure the repair tool 102 onto the surface 105. In yet another embodiment, an adhesive can be utilized to secure the repair tool 102 onto the surface 105, such as a hot melt adhesive, epoxy material, etc. Then, the adhesive material can be melted to remove the repair tool 102 from the surface 105.

Through the attachment mechanism 135, the location of repair tool 102 can be precisely controlled and temporarily secured in place, which allows for precision work to be performed. In one embodiment, a working head 122 is positioned and secured adjacent to the identified defect 106 of the internal engine component(s) 104 being repaired (e.g., a turbine blade(s)). For example, as particularly shown in FIG. 4, the defect 106 corresponds to a crack, void or other defective area formed along the exterior of the component 104 that defines an open or fillable volume 108 with a base 107 of the crack, void or other defective area.

Figure 7:
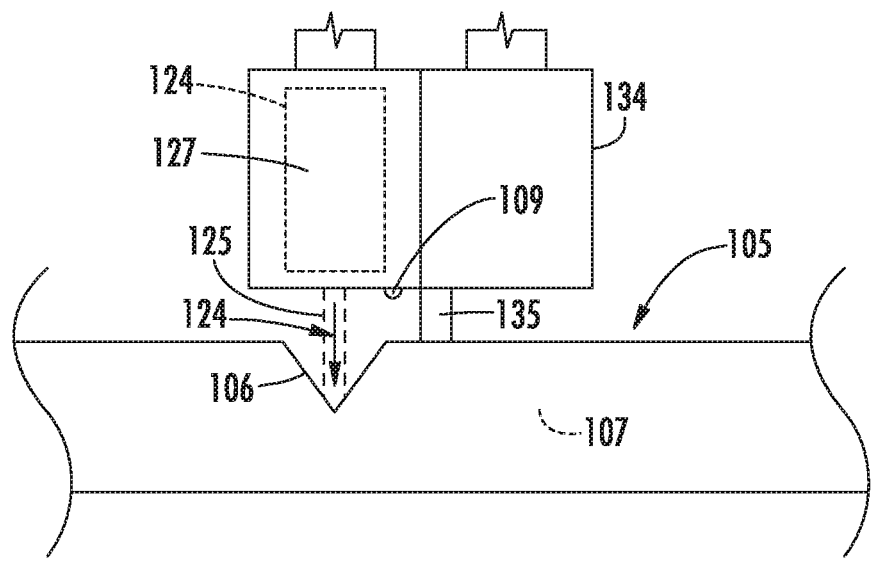
FIG. 7 illustrates a partial view of one embodiment of the repair tool temporarily secured to a surface of an internal component of the gas turbine engine in order to supply powder particles within a defect for in situ repair.

As shown in FIGS. 5-9, the working head 122 includes a work mechanism 124 configured for addressing the defect 106. In one embodiment, the new material can be supplied from a location exterior to the engine to the internal location of the defect 106 to allow the fillable volume 108 defined by the defect 106 to be filled with the new material. FIG. 7 shows the repair tool 102 configured to supply high velocity powder particles 125 from the exterior of the engine into the fillable volume 108 of the defect 106. Upon impacting a surface of the defect 106, the high velocity particles 125 may plastically deform and adhere to the surface, thereby filling-in the fillable volume 108 and repairing the defect 106. For example, the particles can impact the surface within the defect 106 at a speed of about 150 meters per second (m/s) to about 900 m/s.

The average size of the powder particles 125 can vary depending on their composition, gun type, nozzle type, gases used, etc. In most embodiments, the particle size and distribution can be about 25 µm to about 150 µm (e.g., about 35 µm to about 75 µm (i.e., 400 to about 200 mesh)). In certain embodiments, no more than about five percent of the particles are larger than about 75 µm (200 mesh) and no more than about fifteen percent of the particles being smaller than about 35 µm (400 mesh).

The powder particles 125 can be supplied to the location of the defect via the repair tool 102 such that the fillable volume 108 may be filled-in with the powder particles 125, thereby repairing the defect 106. In several embodiments, the repair tool 102 may be configured to supply the powder particles 125 within the interior of the gas turbine engine 10. For example, the powder particles 125 may be transported via the repair tool 102 from a location exterior to the gas turbine engine 10 to a location within the engine 10 to allow the powder particles 125 to be injected or otherwise directed into the fillable volume 108 defined by the defect 106.

The particles 125 may be supplied via a carrier fluid (e.g., a carrier gas) that is inert to the coating deposition.

Figure 8:
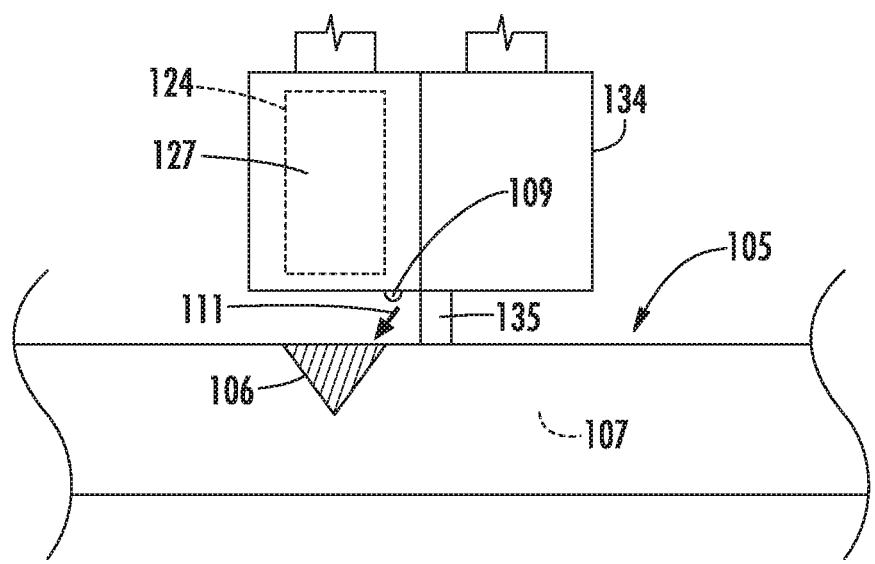
FIG. 8 illustrates a partial view of the embodiment of the repair tool of FIG. 8 using a laser to weld the powder particles within the defect.

The powder particles 125 may then be heated to fuse the material within the fillable volume 108 to repair the defect 106. For example, the repair tool 102 may include a laser 109 at its working end to heat the powder particles 125 during and/or after introduction into the defect 106, thereby filling in the fillable volume 108 to bond the material within the defect 106. For example, the working head 122 may include a laser 109 directed into the flow path of the powder particles 125 (e.g., into the defect 106) to locally heat the base of the defect 106, before, during, and/or after deposition of the new material (e.g., the powder particles 125). For example, the laser 109 may direct electromagnetic radiation 111 having a wavelength of about 0.5 µm to about 25 µm into the defect 106 in the surface 105 of the component 104 at a power level of about 0.02 W to about 75 kW. The electromagnetic radiation 111 can heat a precision weld within the base 107 of the defect 106 (e.g., at the deepest point from the surface 105 within the component 104) to effectively stop the propagation of the defect 106 through the component 104. FIG. 8 shows the laser 109 directing electromagnetic radiation 111 onto the new material within the defect 106.

For example, the base 107 may be locally heated using the laser 109 to a temperature of about 1000° C. to about 2000° C. (e.g., about 1800° C. to about 2000° C.), particularly with the component 104 is constructed from a metal alloy or super-alloy such as a nickel-based alloy, a chromium-based alloy, etc.

Figure 9:
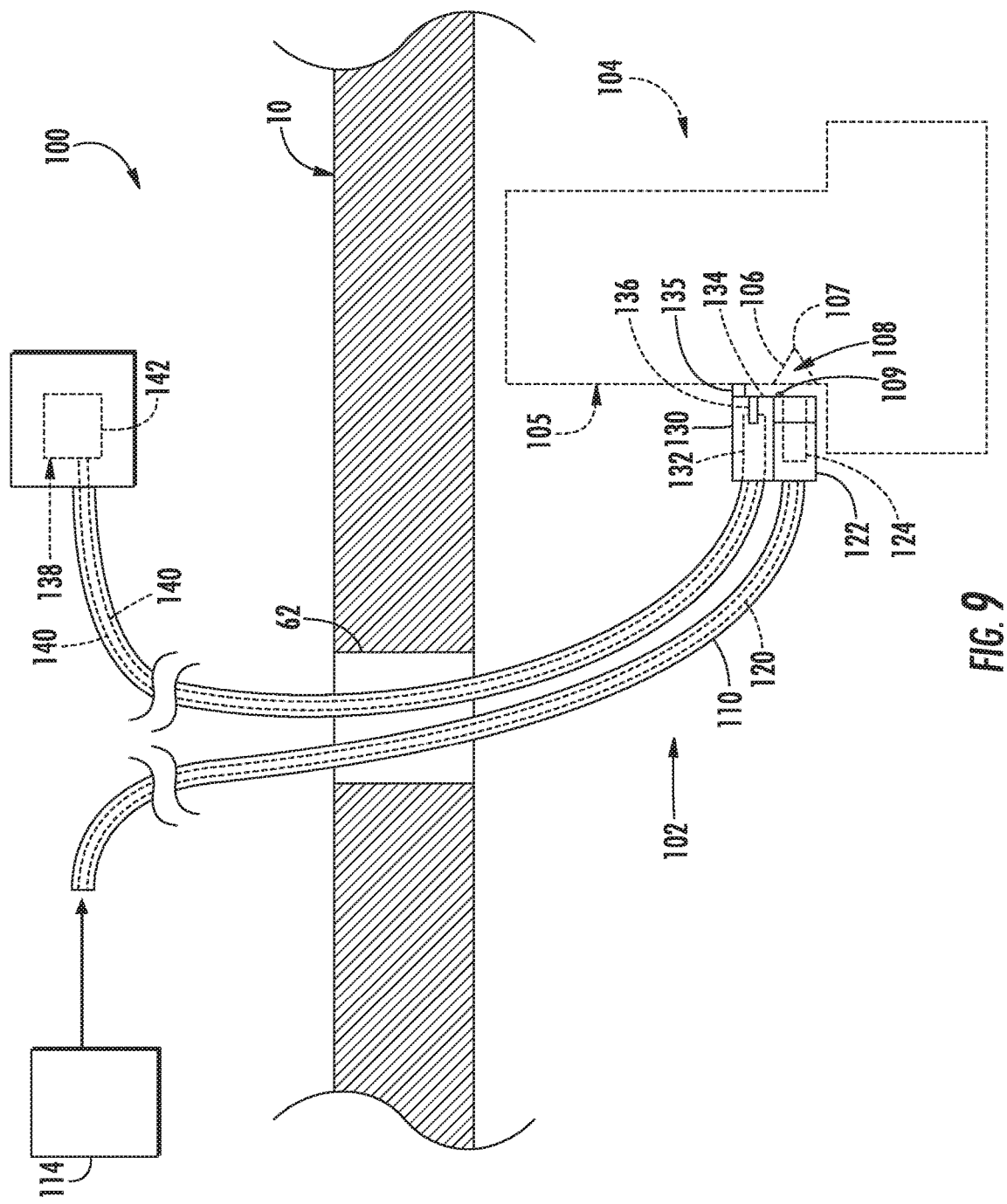
FIG. 9 illustrates a simplified view of one embodiment of a system for performing an in situ repair of an internal component of a gas turbine engine in accordance with aspects of the present subject matter, particularly illustrating a repair tool inserted through an access port of the engine to access a defect of the internal component and supply a fill material into a defect on the component.

In one embodiment, the repair tool 102 may include one or more heating elements (indicated by dashed lines 120) provided in operative association within the high temperature conduit 110. As shown in the illustrated embodiment of FIG. 9, the repair tool 102 may include a high temperature conduit 110 for transporting the metal particles from outside the engine 10 to the location of the defect 106. Specifically, as shown in FIG. 9, the high temperature conduit 110 may extend lengthwise between working head 122 located within the gas turbine engine 10 and a material supply end 114 located exterior to the engine 10. The tip end of the tool 102 may generally be positioned adjacent to the location of the defect 106 for directing the particles 125 into the fillable volume 108. Additionally, the material supply end 114 of the tool 102 may generally be configured to receive particles 125 from a particle source. For example, as shown in FIG. 9, particles 125 contained within a chamber (or other suitable powder particle source) located exterior to the gas turbine engine 10 may be supplied to the material supply end 114 of the tool 102. The particles 125 received at the material supply end 114 may then be directed through the high temperature conduit 110 to the tip end of the tool 102 to allow the metal particles to be delivered to the location of the defect 106.

It should be appreciated that the high temperature conduit 110 may generally be formed from any suitable high temperature material that allows the conduit 110 to serve as a fluid delivery means for the liquid metal. For example, in several embodiments, the high temperature conduit 110 may be formed from a ceramic material capable of withstanding temperatures above the melting temperature of the metal being supplied to the defect 106. However, in other embodiments, the conduit 110 may be formed from any other suitable high temperature material.

In general, the heating element(s) 120 may be configured to generate heat within the high temperature conduit 110 as powder particles 125 is being supplied through the conduit 110 so as to allow for particle flow at the desired rate and speed. For example, in one embodiment, the heating element(s) 120 may correspond to a resisting heating element(s), such as one or more resistance wires, that is integrated into or incorporated within a wall(s) of the conduit 110. However, in another embodiment, the heating element(s) 120 may correspond to any other suitable heat generating device(s) and/or component(s) that may be used to provide heating within the conduit 110 so as to maintain the temperature of the powder particles 125 at its desired delivery temperature. In one embodiment, the particles 125 are delivered to the defect 106 at a temperature within 25% of its melting point (e.g., within 10% of its melting point).

It should be appreciated that the powder particles 125 may be composed of any suitable metal material. For example, in one embodiment, the powder particles 125 may correspond to the parent metal material of the internal component 104 being repaired. In other embodiments, the powder particles 125 may correspond to any other metal material that is suitable for use as a repair material within a gas turbine engine 10.

In one embodiment, the repair tool 102 includes an optical probe 130 adjacent to the working head 122 and configured to be used in association with the repair tool 102. For instance, as shown in FIG. 4, the optical probe 130 corresponds to a separate component configured to be used in combination with the repair tool 102 for repairing the defect 106. However, in other embodiments, the optical probe 130 may be coupled to or integrated within the repair tool 102. Additionally, as shown in FIG. 4, the optical probe 130 has been inserted through the same access port 62 as the repair tool 102. However, in other embodiments, the probe 130 may be inserted into a different access port 62 than the repair tool 102, such as an access port 62 located adjacent to the access port 62 within which the repair tool 102 has been inserted.

In general, the optical probe 130 may correspond to any suitable optical device that allows images of the interior of the engine 10 to be captured or otherwise obtained. For instance, in several embodiments, the optical probe 130 may correspond to a borescope, videoscope, fiberscope or any other similar optical device known in the art that allows for the interior of a gas turbine engine 10 to be viewed through an access port 62. In such embodiments, the optical probe 130 may include one or more optical elements (indicated schematically by dashed box 132), such as one or more optical lenses, optical fibers, image capture devices, cables, and/or the like, for obtaining views or images of the interior of the engine 10 at a tip 134 of the probe 130 and for transmitting or relaying such images from the probe tip 134 along the length of the probe 130 to the exterior of the engine 10 for viewing by the personnel performing the repair procedure on the internal component(s) 104. In addition, the probe 130 may include a light source (indicated by dashed box 136) positioned at or adjacent to the probe tip 134 to provide lighting within the interior of the engine 10.

As shown in FIGS. 4 and 9, the optical probe 130 may also include an articulation assembly 138 that allows the orientation of the probe tip 134 to be adjusted within the interior of the gas turbine engine 10. For example, the articulation assembly 138 may allow for the probe tip 134 to be rotated or pivoted about a single axis or multiple axes to adjust the orientation of the tip 134 relative to the remainder of the probe 130. It should be appreciated that the articulation assembly 138 may generally have any suitable configuration and/or may include any suitable components that allow for adjustment of the orientation of the probe tip 134 relative to the remainder of the probe 130. For example, in one embodiment, a plurality of articulation cables 140 may be coupled between the probe tip 134 and one or more articulation motors 142. In such an embodiment, by adjusting the tension of the cables 140 via the motor(s) 142, the probe tip 134 may be reoriented within the gas turbine engine 10.

In one particular embodiment, the articulation assembly 138 also controls the attachment mechanism 135 so as to temporarily attach to the surface 105 the component 104 in order to perform the desired work thereon.

Methods are generally provided for performing an in situ repair of an internal component of a gas turbine engine. In general, the methods are discussed herein with reference to the gas turbine engine 10 and the system 100 described above with reference to FIGS. 1-9. However, it should be appreciated by those of ordinary skill in the art that the disclosed methods may generally be implemented with gas turbine engines having any other suitable engine configuration and/or with systems having any other suitable system configuration. In addition, although the methods are discussed in a particular order for purposes of discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

The method may include inserting a repair tool through an access port of the gas turbine engine such that the tool includes a tip end positioned within the engine; positioning the tip adjacent to a defect (e.g., a crack or other distress point) within the surface of the component; and temporarily attaching the tip adjacent to the defect to allow precision work to be performed. For example, as indicated above, the method may include positioning the tip end of the repair tool adjacent to a defect of an internal component of the gas turbine engine. As indicated above, the defect 106 may, for example, correspond to a crack, void or other defective area of an internal component 104 of the gas turbine engine 10.

Moreover, the method may include performing precision repair work (e.g., supplying powder particles, heating, etc.) using the repair tool by temporarily attaching the tip end of the repair tool to the surface of the component.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method of in situ material build-up on a tip of a blade of a gas turbine engine, the method comprising:
   inserting a working head through an access port of an assembled core gas turbine engine, wherein the working head comprises a laser and a tripod grip;
   inserting a material supply adjacent to the tip of the blade-while the blade is an installed internal component of the gas turbine engine, such that the material supply is positioned radially inwardly of a shroud of the gas turbine engine;
   positioning the working head adjacent to an interface defined between the material supply and the tip of the blade;

temporarily securing the working head adjacent to the blade with the tripod grip, wherein the tip of the blade has a known shape and size, and wherein the tripod grip comprises a plurality of grip arms oriented to grip the tip of the blade having the known shape and size within the gas turbine engine; and directing a radiation from the laser onto the interface of the material supply and the tip of the blade such that the material supply melts and attaches to the tip of the blade.

2. The method of claim 1, wherein the radiation has a wavelength of about 0.5 μm to about 25 μm.

3. The method of claim 1, wherein the laser emits electromagnetic radiation at a power level of about 0.02 W to about 75 kW.

4. The method of claim 1, wherein the working head is attached to a robotic arm.

5. The method of claim 4, wherein the interface precision is 0.05 inches or less.

6. The method of claim 4, wherein an optical probe is attached to the robotic arm.

7. The method of claim 1, further comprising:

inserting an optical probe through the access port or an adjacent access port of the gas turbine engine, the optical probe being configured to provide a view of the interface within the gas turbine engine.

8. A method of in situ material build-up on a tip of a blade of a gas turbine engine, the method comprising:

inserting a working head through an access port of an assembled core gas turbine engine, wherein the working head comprises a laser, a hot-melt adhesive, and a heating component for melting the hot melt adhesive;

inserting a material supply adjacent to the tip of the blade-while the blade is an installed internal component of the gas turbine engine, such that the material supply is positioned radially inwardly of a shroud of the gas turbine engine;

positioning the working head adjacent to an interface defined between the material supply and the tip of the blade;

temporarily securing the working head adjacent to the blade with the hot-melt adhesive;

directing a radiation from the laser onto the interface of the material supply and the tip of the blade such that the material supply melts and attaches to the tip of the blade; and melting the hot melt adhesive with the heating component to remove the working head from the blade.

9. The method of claim 8, wherein the radiation has a wavelength of about 0.5 μm to about 25 μm.

10. The method of claim 8, wherein the radiation is electromagnetic radiation emitted from the laser at a power level of about 0.02 W to about 75 kW.

11. The method of claim 8, wherein the working head is attached to a robotic arm.

12. The method of claim 11, wherein the interface precision is 0.05 inches or less.

13. The method of claim 11, wherein an optical probe is attached to the robotic arm.

14. The method of claim 8, further comprising:

inserting an optical probe through the access port or an adjacent access port of the gas turbine engine, the optical probe being configured to provide a view of the interface within the gas turbine engine.

* * * * *